United States Patent
Kim et al.

(10) Patent No.: US 11,273,196 B2
(45) Date of Patent: Mar. 15, 2022

(54) **ANTITHROMBOTIC COMPOSITION CONTAINING *POLYGONUM CUSPIDATUM* SIEB. ET ZUCC. AND *CINNAMOMUM CASSIA* BLUME**

(71) Applicants: National Institute for Korean Medicine Development, Gyeongsangbuk-do (KR); NovMetaPharma Co., Ltd., Seoul (KR)

(72) Inventors: Hyo Jung Kim, Daegu (KR); Sun Gun Kim, Busan (KR); Jai Hyun So, Daegu (KR); Hwa Dong Lee, Gyeongsangbuk-do (KR); Hye Ryung Kang, Busan (KR)

(73) Assignees: NATIONAL INSTITUTE FOR KOREAN MEDICINE DEVELOPMENT, Gyeongsangbuk-do (KR); NOVMETAPHARMA CO., LTD., Seoul (KR)

( * ) Notice: Subject to any disclaimer, the term of this patent is extended or adjusted under 35 U.S.C. 154(b) by 198 days.

(21) Appl. No.: 16/759,554

(22) PCT Filed: Sep. 20, 2018

(86) PCT No.: PCT/KR2018/011130
§ 371 (c)(1),
(2) Date: Apr. 27, 2020

(87) PCT Pub. No.: WO2019/083168
PCT Pub. Date: May 2, 2019

(65) Prior Publication Data
US 2020/0282000 A1 Sep. 10, 2020

(30) Foreign Application Priority Data
Oct. 27, 2017 (KR) ........................ 10-2017-0141167

(51) Int. Cl.
*A61K 36/704* (2006.01)
*A61K 9/00* (2006.01)
*A61K 36/54* (2006.01)

(52) U.S. Cl.
CPC .......... *A61K 36/704* (2013.01); *A61K 9/0056* (2013.01); *A61K 36/54* (2013.01)

(58) Field of Classification Search
CPC .. A61K 2300/00; A61K 36/704; A61K 36/54; A61K 36/70; A61K 9/0056; A23L 33/105; A61P 7/02; A61P 9/10; A23V 2002/00; A23V 2200/326
See application file for complete search history.

(56) References Cited

FOREIGN PATENT DOCUMENTS

| KR | 10-0769302 | 10/2007 |
| KR | 10-0784339 | 12/2007 |
| KR | 20160072932 | 6/2016 |

OTHER PUBLICATIONS

Yang, Won Kyung et al., "Antithrombotic Effect and Antiplatelet Activity of Polygonum Cuspidatum Extract", Journal of the Korean Society of Food Science and Nutrition, Feb. 2012.
Patocka, J. et al., "Biolgoically Active Compounds of Knotweed (*Reynoutria* spp.)", Military Medical Science Letters, Mar. 10, 2017.
International Search Report for PCT/KR2018/01130 dated Dec. 27, 2018 (4 pages).

*Primary Examiner* — Aaron J Kosar
(74) *Attorney, Agent, or Firm* — Susan Paik, Esq.

(57) ABSTRACT

The present invention relates to an antithrombotic composition including *Polygonum cuspidatum* Sieb. et Zucc. and *Cinnamomum cassia* Blume as active ingredients, and preferably includes an extract obtained by mixing *Polygonum cuspidatum* Sieb. et Zucc. and *Cinnamomum cassia* Blume in a weight ratio of 1:2-2:1 and extracting the mixture. The composition of the present invention is highly effective in antithrombotic effects, identified as a platelet aggregation inhibitory effect, a thrombosis inhibitory effect, a thrombosis-delaying effect, and the like, and thus can be used as an effective herbal-medicine-based agent for preventing or treating thrombosis, an antithrombotic health food, and the like.

7 Claims, 5 Drawing Sheets

[FIG. 1]
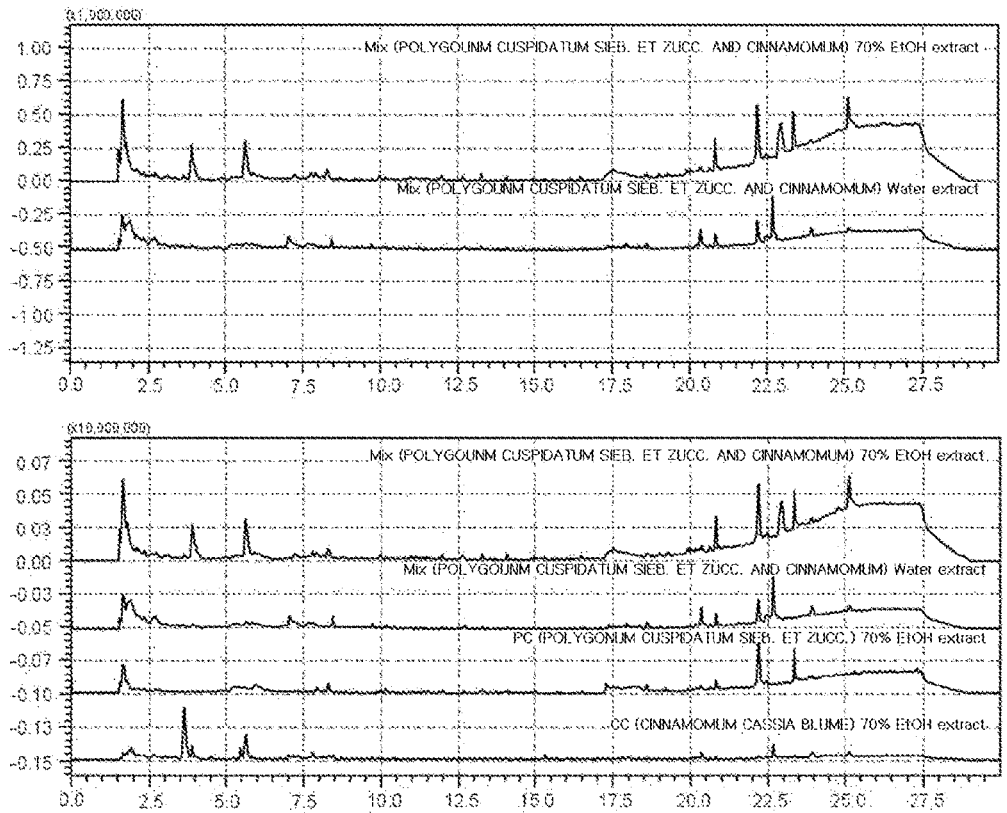

[FIG. 2]
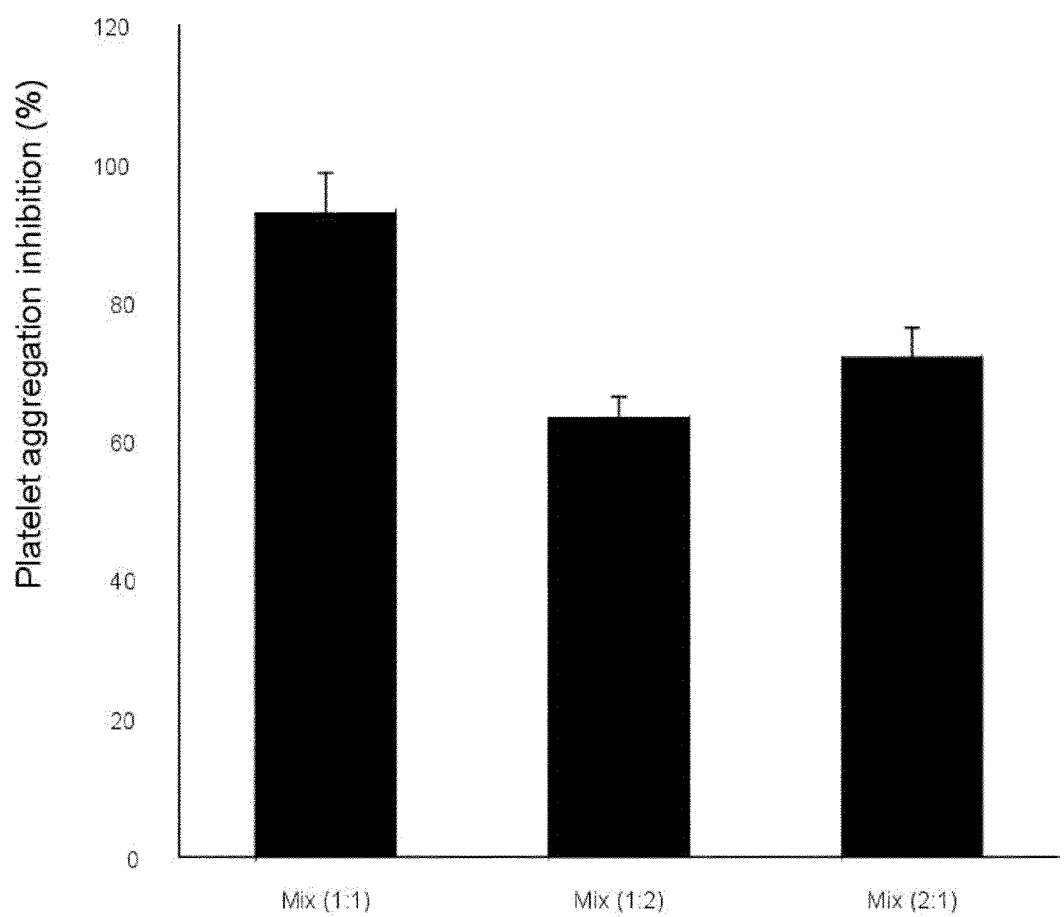

[FIG. 3]
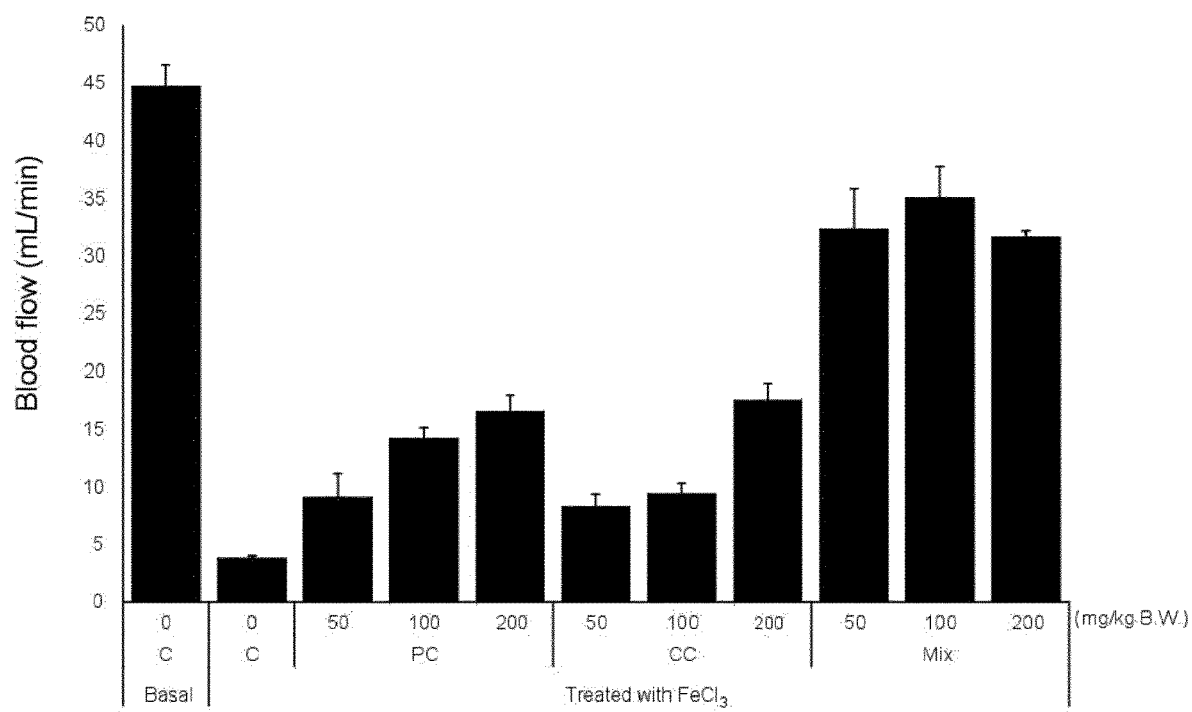

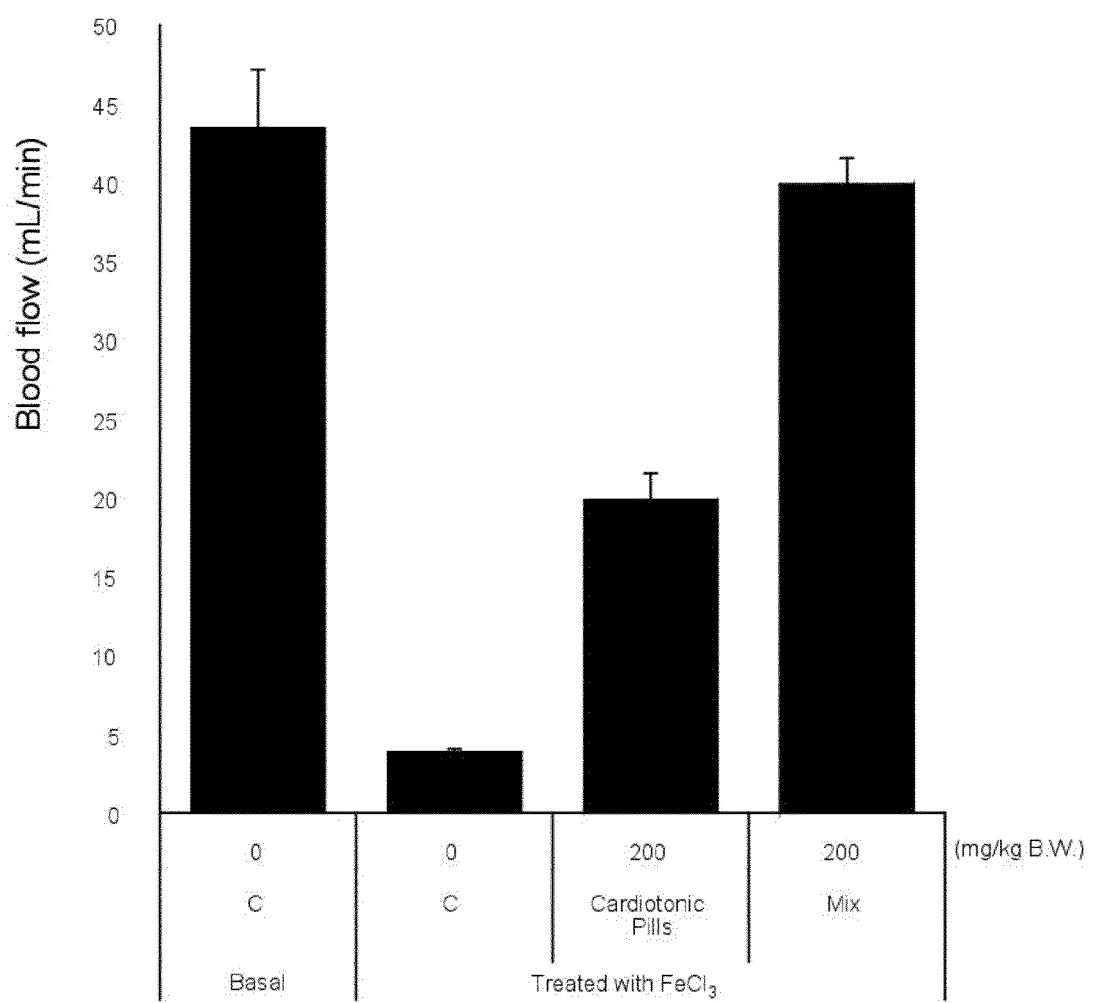
[FIG. 4]

[FIG. 5]
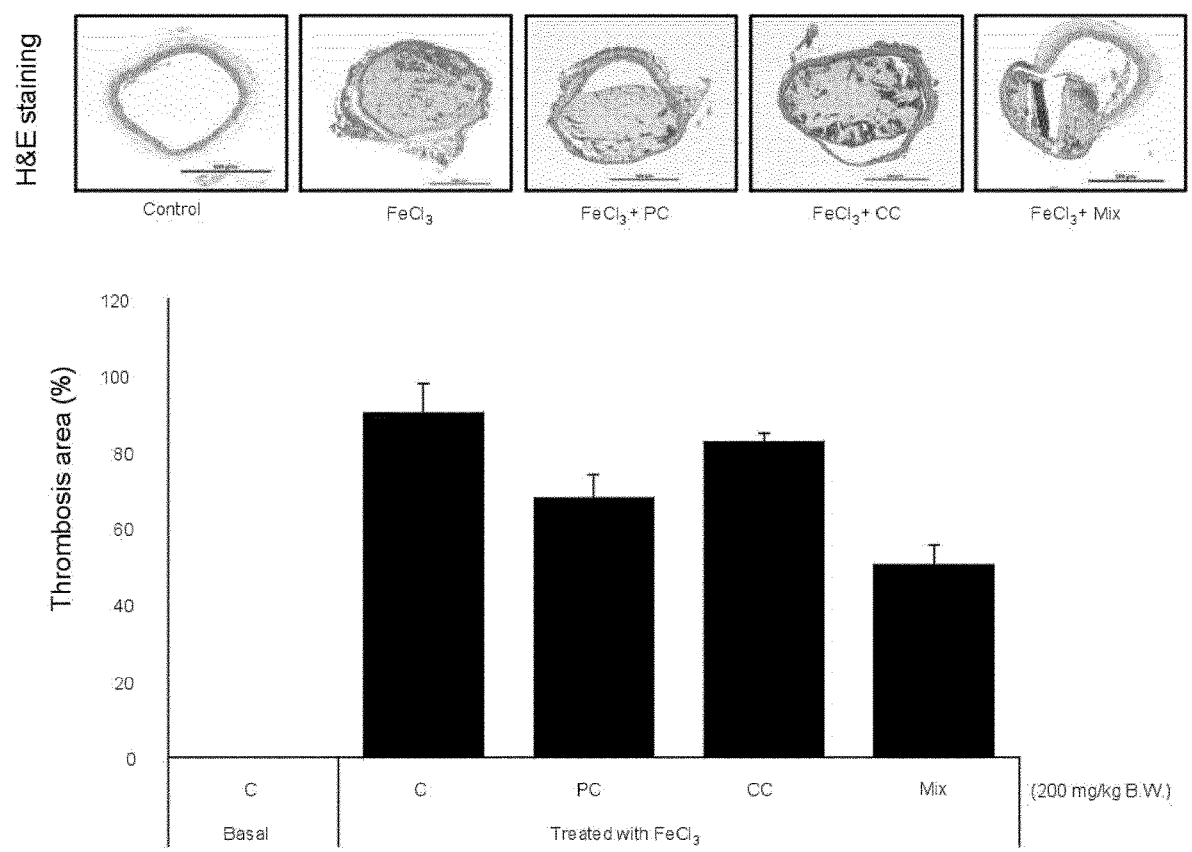

ANTITHROMBOTIC COMPOSITION CONTAINING *POLYGONUM CUSPIDATUM* SIEB. ET ZUCC. AND *CINNAMOMUM CASSIA* BLUME

TECHNICAL FIELD

The present invention relates to an antithrombotic composition including *Polygonum cuspidatum* Sieb. et Zucc. and *Cinnamomum cassia* Blume as active ingredients.

BACKGROUND ART

Recently, as the national income has increased and the quality of consumption has improved, the rate of mortality due to vascular disorders is rapidly increasing. In particular, the morbidity of cardio-cerebrovascular disease due to increases in vascular risk factors, such as arteriosclerosis and thrombosis, continues to increase worldwide.

Since blood coagulation and lysis are always in equilibrium in vivo, blood flow is not disturbed by bleeding, a thrombus, or the like under normal conditions. However, when a blood vessel wall is damaged, this state of equilibrium is broken (Lee H S. How safe is the re-administration of streptokinase, Drug Safety 13, 76-80. 1995).

Arteriosclerosis is a disease that occurs when vascular endothelial cells are damaged by genetic variation, peroxide, hypertension, diabetes, increased plasma homocysteine concentration, microbial infection, and the like. Vascular endothelial cells with dysfunction express cell adhesion molecules and increase cell permeability, allowing immune cells, platelets, lipids, and the like to permeate into tissue. Arteriosclerotic lesions occur due to a series of inflammatory responses, such as the secretion of inflammatory mediators, growth factors, and the like, by immune cells that have penetrated into tissues (Ross R. Atherosclerosis—an inflammatory disease. New Engl. J. Med. 340(2):115-126, 1999). In addition, when the vascular intima is damaged, platelets adhere to the damaged site of vascular tissue, leading to platelet activation by aggregation agonists such as collagen, arachidonic acid, ADP, and thromboxane A2 (TXA2), subsequently causing adhesion, secretion, and aggregation, thereby activating the blood coagulation system and eventually forming a thrombus (Yang S A. et al., Effect of methanolic extract from *Salvia miltiorrhiza* Bunge on in-vitro antithrombotic and antioxidative activities. Korean J. Food Sci. Technol. 39, 83-87. 2007).

Thrombosis is the accumulation of blood clots inside blood vessels, which obstructs the flow of blood, and thus causes disorders in cellular growth and function, and is a major cause of various adult diseases, such as cerebral infarction and myocardial infarction. When a blood clot occurs in a vein, blood circulation disorder is caused, which causes edema or inflammation, and when a blood clot occurs in an artery, it causes ischemia or infarction, leading to cardiovascular diseases such as arteriosclerosis, myocardial infarction, stroke, and pulmonary embolism.

Antiplatelet agents known to date include theophylline, molsidomin, verapamil, nifedipine, aspirin, imidazole, indomethacin, and the like. These drugs are known to inhibit the recruitment of $Ca^{2+}$ by promoting the production of cAMP and cGMP or to inhibit the production of thromboxane A2. However, the use of these drugs is limited due to side effects thereof, such as hemorrhagic side effects, gastrointestinal disorders, infertility, and hypersensitivity reactions.

Therefore, there is a need for an excellent antithrombotic agent that can effectively inhibit thrombosis and minimize side effects on the human body.

Cardiotonic pills are known as a representative medicinal herb composition having an antithrombotic effect. Cardiotonic pills, which are an agent for preventing or treating arteriosclerosis, have vasodilatory, sedative, and analgesic effects, and consist of *Salvia miltiorrhiza*, which has long been used, *Panax notoginseng*, having anti-inflammatory activity, and borneol, having central nervous system excitation and antibacterial activity.

Meanwhile, *Polygonum cuspidatum* Sieb. et Zucc. (*Reynoutria japonica* Hou.), which is a perennial herbaceous plant belonging to the family Polygonaceae, refers to the root or rootstock of *Polygonum cuspidatum* and closely related plants belonging to the same genus, and is also referred to as other Korean names such as "Go-jang," "San-Jang," "Ban-jang," "San-tong-soon," "Ban-jang geun," "Oh-bu-dab," "San-gan," "Ban-geun," "Woong-hwang-yeon," and "To-ji-yu." *Polygonum cuspidatum* Sieb. et Zucc. is distributed in Korea, Japan, Taiwan, China, and the like, and in Korea, it grows in the valleys of mountains and fields nationwide. *Polygonum cuspidatum* Sieb. et Zucc. is 1 m or more in height, the rootstock extends laterally underground and is ligneous and yellowish brown, and the nodes are clear. The stem grows straight in the form of a hollow circle. The surface has no hairs and has many red or purple spots. These root, rootstock and leaf parts have long been used as medicinal herbs. *Polygonum cuspidatum* Sieb. et Zucc. is known as a mitigator, a diuretic, an emmenagogue, an antitussive, and a tranquilizer, and has pharmacological actions such as antibacterial activity and antiviral activity.

*Cinnamomum cassia* Blume, which is an evergreen plant belonging to the family Lauraceae, is the stem bark of cinnamon or other closely related plants belonging to the same genus, from which the main skin and the primary cortex have been removed. It has a long plank shape or cylindrical shape and a length of 10-20 cm, and the thickness thereof is not uniform. Both the outer and inner sides are reddish brown and bend well. The bent side is reddish brown and rich in oil. It has a unique aroma and the taste is spicy and sweet. *Cinnamomum cassia* Blume, which is a strong cardiac agent, is known to have pharmacological actions, such as being effective in overcoming cardiac weakness through promotion of blood circulation, excitability, nurturing of the stomach, promoting intestinal functions, warming and promoting recuperation of the body, promoting the function of the meridian system and pulse flow through warming, erectile dysfunction, body temperature control, strengthening physical constitution, and relieving gas.

LISTING OF PATENT DOCUMENTS (Patent Document 1) Korean Patent Publication No. 10-2017-0086120

(Patent Document 2) Korean Patent Publication No. 10-2016-0058212

LISTING OF NON-PATENT DOCUMENTS (Non-Patent Document 1) Yang Y Y et al., Screening of antioxidative, anti-platelet aggregation and anti-thrombotic effects of Clove extracts. Korean J Oriental Physiology & Pathology. 25(3):471-481, 2011

(Non-Patent Document 2) Lee H S. How safe is the re-administration of streptokinase, Drug Safety 13, 76-80. 1995

(Non-Patent Document 3) Ross R. Atherosclerosis-an inflammatory disease. New Engl. J. Med. 340(2):115-126, 1999

(Non-Patent Document 4) Yang S A. et al., Effect of methanolic extract from *Salvia miltiorrhiza* Bunge on in-vitro antithrombotic and antioxidative activities. Korean J. Food Sci. Technol. 39, 83-87. 2007

SUMMARY OF THE INVENTION

Technical Problem

It is an object of the present invention to provide an antithrombotic composition having excellent thrombosis inhibitory activity using *Polygonum cuspidatum* Sieb. et Zucc. and *Cinnamomum cassia* Blume, which are medicinal herbs.

Technical Solution

In accordance with an aspect of the present invention, the above and other objects can be accomplished by the provision of an antithrombotic composition including *Polygonum cuspidatum* Sieb. et Zucc. and *Cinnamomum cassia* Blume as active ingredients.

In the composition, the *Polygonum cuspidatum* Sieb. et Zucc. and the *Cinnamomum cassia* Blume are preferably an extract obtained by mixing in a weight ratio of 1:2-2:1 and through extraction. More preferably, the *Polygonum cuspidatum* Sieb. et Zucc. and the *Cinnamomum cassia* Blume are an extract obtained by mixing in a weight ratio of 1:1 and through extraction.

In the composition, the extract is preferably obtained by adding an extraction solvent at a volume that is 150 times to 250 times that of the mixture of the *Polygonum cuspidatum* Sieb. et Zucc. and the *Cinnamomum cassia* Blume, followed by immersion at 50° C. to 70° C. for 22 hours to 26 hours, thereby obtaining an extract, filtering the extract, concentrating the filtrate under reduced pressure, and drying the concentrate.

In the composition, the solvent is preferably 70% ethanol.

In accordance with another aspect of the present invention, there is provided an agent for preventing or treating thrombosis, which includes the above-described composition as an active ingredient.

In accordance with a further aspect of the present invention, there is provided an antithrombotic health food including the above-described composition.

Advantageous Effects

According to the present invention, an antithrombotic composition including *Polygonum cuspidatum* Sieb. et Zucc. and *Cinnamomum cassia* Blume is highly effective in antithrombotic effects, identified as a platelet aggregation inhibitory effect, a thrombosis inhibitory effect, a thrombosis-delaying effect, and the like, compared to cardiotonic pills which are currently commercially available as antithrombotic medicinal herb compositions. The antithrombotic composition of the present invention has the effects of preventing or treating cardiovascular diseases that may be caused by thrombi, such as arteriosclerosis, cerebral infarction, myocardial infarction, stroke, and pulmonary embolism, and thus can be used as an effective herbal-medicine-based agent for preventing or treating thrombosis, an antithrombotic health food, and the like.

BRIEF DESCRIPTION OF THE DRAWINGS

FIG. 1 illustrates GC-MS analysis results of confirming the extracted components of a mixed extract of *Polygonum cuspidatum* Sieb. et Zucc. and *Cinnamomum cassia* Blume.

FIG. 2 illustrates the results of confirming the inhibitory effect of a composition of the present invention on a platelet aggregation phase induced by collagen.

FIGS. 3 and 4 illustrate the results of confirming the effect of a composition of the present invention on delaying thrombosis in a thrombogenic animal model.

FIG. 5 illustrates the results of confirming histological changes in blood vessels in a thrombogenic animal model.

DETAILED DESCRIPTION OF THE INVENTION

An antithrombotic composition of the present invention includes, as active ingredients, *Polygonum cuspidatum* Sieb. et Zucc. and *Cinnamomum cassia* Blume, and preferably includes an extract obtained by mixing *Polygonum cuspidatum* Sieb. et Zucc. and *Cinnamomum cassia* Blume in a weight ratio of 1:2-2:1 and extracting the mixture. Particularly preferably, the composition includes an extract obtained by mixing *Polygonum cuspidatum* Sieb. et Zucc. and *Cinnamomum cassia* Blume in a weight ratio of 1:1 and extracting the mixture.

It is preferable to use water or ethanol as a solvent for extraction. It is particularly preferable to use 70% ethanol as an extraction solvent. When 70% ethanol is used as the extraction solvent, more components are extracted than when water is used as the extraction solvent (see FIG. 1).

In addition, the extract obtained by mixing *Polygonum cuspidatum* Sieb. et Zucc. and *Cinnamomum cassia* Blume and extracting the mixture includes all components of an extract obtained by extracting each of *Polygonum cuspidatum* Sieb. et Zucc. and *Cinnamomum cassia* Blume, and also additionally includes other components (see FIG. 1).

The extraction of *Polygonum cuspidatum* Sieb. et Zucc. and *Cinnamomum cassia* Blume may be performed using a general extraction method, and examples of a preferable extraction method are as follows.

An extraction solvent is added to the mixture of *Polygonum cuspidatum* Sieb. et Zucc. and *Cinnamomum cassia* Blume at a volume that is 150 times to 250 times that of the mixture, the mixture is immersed therein at 50° C. to 70° C. for 22 hours to 26 hours, and then an extract is obtained at room temperature. This process may be repeated two or three times. After filtering the extract, the filtrate is concentrated under reduced pressure and dried to obtain a mixed extract of *Polygonum cuspidatum* Sieb. et Zucc. and *Cinnamomum cassia* Blume.

The antithrombotic composition of the present invention is highly effective in antithrombotic effects, identified as a platelet aggregation inhibitory effect, a thrombosis inhibitory effect, a thrombosis-delaying effect, and the like. In particular, compared to the case of using either *Polygonum cuspidatum* Sieb. et Zucc. or *Cinnamomum cassia* Blume alone, the effect is much stronger, and the thrombosis-delaying effect is about twice as strong as that of cardiotonic pills, which are currently commercially available as an antithrombotic medicinal herb composition. Therefore, the antithrombotic composition of the present invention may be used as an effective herbal-medicine-based agent for preventing or treating thrombosis, an antithrombotic health food, and the like.

A dried extract of *Polygonum cuspidatum* Sieb. et Zucc. and *Cinnamomum cassia* Blume of the antithrombotic composition of the preset invention may be used in an amount of 100 mg to 1,000 mg daily based on an adult body weight of 60 kg when used for the prevention of thrombosis, and in an amount of 500 mg to 5,000 mg daily when used for the treatment of thrombosis.

Hereinafter, the present invention will be described in further detail with reference to the following examples. These examples are provided for illustrative purposes only and are not intended to limit the scope of the present invention.

EXAMPLES

Example 1

Preparation of Mixed Extract of *Polygonum cuspidatum* Sieb. et Zucc. and *Cinnamomum cassia* Blume 20 l of 70% ethanol was added to 100 g of *Polygonum cuspidatum* Sieb. et Zucc. and 100 g of *Cinnamomum cassia* Blume, which were purchased from Human Herb (http://www.humanherb.co.kr/), followed by immersion therein at 60° C. for 24 hours, and then an extract was obtained at room temperature. Again, 20 l of 70% ethanol was added, and the extraction process was repeated twice more to collect the extract.

The filtrate obtained by filtering each extract was concentrated under reduced pressure by evaporating the solvent in a vacuum rotary evaporator (Nihon Seiko, Japan, VR-205c) and dried to obtain 41.8 g of a mixed extract of *Polygonum cuspidatum* Sieb. et Zucc. and *Cinnamomum cassia* Blume (yield: 20.9%).

Example 2

Preparation of Mixed Extract of *Polygonum cuspidatum* Sieb. et Zucc. and *Cinnamomum cassia* Blume A 1:2 mixed extract of *Polygonum cuspidatum* Sieb. et Zucc. and *Cinnamomum cassia* Blume was obtained in the same manner as in Example 1, except that 66.7 g of *Polygonum cuspidatum* Sieb. et Zucc. and 133.3 g of *Cinnamomum cassia* Blume were used.

Example 3

Preparation of Mixed Extract of *Polygonum cuspidatum* Sieb. et Zucc. and *Cinnamomum cassia* Blume A 2:1 mixed extract of *Polygonum cuspidatum* Sieb. et Zucc. and *Cinnamomum cassia* Blume was obtained in the same manner as in Example 1, except that 133.3 g of *Polygonum cuspidatum* Sieb. et Zucc. and 66.7 g of *Cinnamomum cassia* Blume were used.

Experimental Example 1

Experiment for Platelet Aggregation Inhibitory Activity

The aggregation of rat platelets was induced using collagen, and the ability of the composition of the present invention to inhibit platelet aggregation depending on the mixing ratio of *Polygonum cuspidatum* Sieb. et Zucc. and *Cinnamomum cassia* Blume was compared as follows.

In the experiment, SD rats (Sprague-Dawley rats, male, 220 g) supplied from KOATECH were used.

The SD rats had an acclimation period of 1 week, and then blood was collected from the abdominal aorta. 2 ml of thyroid buffer (137 mM NaCl, 12 mM $NaHCO_3$, 5.5 mM glucose, 1 M $MgCl_2$, 1 M KCl, and 1 M $Na_2HPO_4$, pH 7.4) was added to 5 ml of the collected blood, followed by centrifugation at 1,000 rpm for 10 minutes.

The supernatant (platelet rich plasma; PRP) from which blood cells had been removed was centrifuged at 800×g for 15 minutes, and the precipitated platelets were washed twice with washing buffer (137 mM NaCl, 2.9 mM KCl, 1 mM $MgCl_2$, 5 mM glucose, 12 mM $NaHCO_3$, 0.34 mM $Na_2HPO_4$, 1 mM EDTA, 20 mM HEPES, and 0.25% BSA, pH 7.4) and then suspended with a suspension buffer (137 mM NaCl, 2.9 mM KCl, 1 mM $MgCl_2$, 5 mM glucose, 12 mM $NaHCO_3$, 0.34 mM $Na_2HPO_4$, 20 mM HEPES, and 0.25% BSA, pH 7.4) to thereby obtain final washed platelets. The obtained washed platelets were diluted to $3 \times 10^8$ platelets/ml and used for analysis.

The platelets were incubated at 37° C. for 3 minutes, 1 mM $CaCl_2$ was then added thereto, and then 100 µg/ml of each of the sample of Example 1 (1:1 mixed extract of *Polygonum cuspidatum* Sieb. et Zucc. and *Cinnamomum cassia* Blume), the sample of Example 2 (1:2 mixed extract of *Polygonum cuspidatum* Sieb. et Zucc. and *Cinnamomum cassia* Blume), and the sample of Example 3 (2:1 mixed extract of *Polygonum cuspidatum* Sieb. et Zucc. and *Cinnamomum cassia* Blume) was added thereto, followed by incubation for 2 minutes.

After incubation, 2.5 µg/ml of collagen, which is an inducer for platelet aggregation, was added to measure the degree of platelet aggregation for 5 minutes. The rat platelet aggregation inhibitory capacity was confirmed by a turbidity measurement method using an aggregometer (Chrono-Log Co., Ltd., Havertown, Pa. USA). The results thereof are illustrated in FIG. 2.

As can be seen from the results of FIG. 2, all of the samples of Examples 1 to 3 exhibited excellent platelet aggregation inhibitory capacity, i.e., 63% or more. In particular, the sample of Example 1 (92.8±5.9%), which is a 1:1 mixed extract of *Polygunum cuspidatum* Sieb. et Zucc. and *Cinnamomum cassia* Blume, exhibited a very potent platelet aggregation inhibitory capacity compared to the sample of Example 2 (63.3±3.1%), which is a 1:2 mixed extract of *Polygunum cuspidatum* Sieb. et Zucc. and *Cinnamomum cassia* Blume, and the sample of Example 3 (72.0±4.4%), which is a 2:1 mixed extract of *Polygunum cuspidatum* Sieb. et Zucc. and *Cinnamomum cassia* Blume.

Experimental Example 2

Confirmation of Effect on Blood Flow Changes in Carotid Artery Thrombus-Induced Animal Model The effects of a *Polygunum cuspidatum* Sieb. et Zucc. extract, a *Cinnamomum cassia* Blume extract, and a mixed extract of *Polygunum cuspidatum* Sieb. et Zucc. and *Cinnamomum cassia* Blume on blood flow changes in an animal model with carotid artery thrombi induced using ferric chloride ($FeCl_3$) were measured as follows.

As an experimental animal, male SD rats (Sprague-Dawley rats, 8 weeks old, 230-250 g, KOATECH, Korea) were purchased, had an acclimation period of 1 week, and were then used for the experiment.

1. Comparison between Single Extract and Mixed Extract

As a sample, the mixed extract of *Polygonum cuspidatum* Sieb. et Zucc. and *Cinnamomum cassia* Blume of Example 1 was used. As samples for comparison, a *Polygonum cuspidatum* Sieb. et Zucc. extract and a *Cinnamomum cassia*

Blume extract were used. The *Polygunum cuspidatum* Sieb. et Zucc. extract and the *Cinnamomum cassia* Blume extract were obtained in the same manner as in Example 1, except that 200 g of *Polygunum cuspidatum* Sieb. et Zucc. and 200 g of *Cinnamomum cassia* Blume were respectively used.

Each sample was orally administered to experimental animals at doses of 50 mg, 100 mg, and 200 mg per 1 kg of body weight for 3 days, and as a control, the same amount of saline was administered. During the test period, experimental animals were allowed to freely eat solid feed and drink water, and the breeding environment was automatically maintained at a temperature of 23±0.5° C. and a relative humidity of 50±50% under 12 hour light/dark cycles.

To anesthetize the experimental animals, an anesthetic in which rompun and Zoletil were mixed at a ratio of 2:3 was used.

To induce carotid artery thrombi in the experimental animals, filter paper (2×2 mm) soaked with a 30% iron chloride solution was brought into contact with the carotid artery for 3 minutes, followed by removal of the filter paper and wiping with physiological saline, and then blood flow was measured using a blood flow measurer (Laser Doppler Flowmetry (LDF); BFL21, Transonic Instrument, USA) equipped with a probe (Powerlab/8sp, ADInstruments Pty Ltd, Castle Hill, NSW, Australia).

After treatment with iron chloride, thrombosis was based on the time at which a blood measurement value dropped near zero, and measured up to 40 minutes in the case of a normal control. The results thereof are illustrated in FIG. 3.

In the normal group (C Basal), no thrombus was produced within a total observation time of 40 minutes, and the group treated with iron chloride was found to have a blood flow value of 0, 17 minutes after treatment with iron chloride.

The group (PC) administered with the *Polygonum cuspidatum* Sieb. et Zucc. extract and the group (CC) administered with the *Cinnamomum cassia* Blume extract exhibited a blood flow value corresponding to about 40% of that of the normal group 40 minutes after treatment with iron chloride, whereas the group (Mix) administered with the mixed extract of *Polygunum cuspidatum* Sieb. et Zucc. and *Cinnamomum cassia* Blume maintained a blood flow value corresponding to about 70% of that of the normal group.

As such, it was confirmed that the extract obtained by mixing *Polygunum cuspidatum* Sieb. et Zucc. and *Cinnamomum cassia* Blume and extracting the mixture exhibited a significantly strong antithrombotic effect compared to a *Polygunum cuspidatum* Sieb. et Zucc. extract or *Cinnamomum cassia* Blume extract alone.

2. Comparison between Mixed Extract and Commercially Available Drug

To compare the effect of the mixed extract of *Polygunum cuspidatum* Sieb. et Zucc. and *Cinnamomum cassia* Blume on a blood flow change, with that of a commercially available drug, an experiment was conducted as follows.

As a commercially available drug, cardiotonic pills (17.5 mg of *Salvia miltiorrhiza*, 3.4 mg of *Panax notoginseng*, and 0.2 mg of borneol) were used.

An experiment was conducted in the same manner as described above, except that the mixed extract of *Polygonum cuspidatum* Sieb. et Zucc. and *Cinnamomum cassia* Blume and cardiotonic pills were orally administered to experimental animals at a dose of 200 mg/kg (body weight). The results thereof are illustrated in FIG. 4.

As can be confirmed in FIG. 4, both the group (Mix) administered with the mixed extract of *Polygonum cuspidatum* Sieb. et Zucc. and *Cinnamomum cassia* Blume and the group administered with cardiotonic pills exhibited a remarkable thrombosis-delaying effect, and particularly, the group (Mix) administered with the mixed extract of *Polygonum cuspidatum* Sieb. et Zucc. and *Cinnamomum cassia* Blume exhibited a thrombosis-delaying effect that was approximately twice that of the group administered with cardiotonic pills. Such a thrombosis inhibitory effect of the mixed extract of *Polygunum cuspidatum* Sieb. et Zucc. and *Cinnamomum cassia* Blume was found to be similar to that of the normal group.

Experimental Example 3

Confirmation of Histological Changes in Blood Vessels in Thrombogenic Animal Model Histological changes in blood vessels of a thrombogenic animal model were confirmed as follows.

After measuring thrombosis in Experimental Example 2, the carotid artery site where the thrombus was generated was extracted to a size of 3 mm to 4 mm.

The extracted carotid artery site was fixed in 10% neutral paraformaldehyde for 24 hours, embedded in paraffin through a normal tissue treatment process, and then sectioned (4 μm thick). The produced sections were stained with hematoxylin & eosin to prepare a tissue specimen for an optical microscope.

The specimen was observed using an optical microscope, and the results thereof are shown in FIG. 5.

As can be confirmed in FIG. 5, the blood vessel of the group treated with iron chloride ($FeCl_3$) was completely filled with a blood clot. In contrast, the group ($FeCl_3$+Mix) administered with the mixed extract of *Polygonum cuspidatum* Sieb. et Zucc. and *Cinnamomum cassia* Blume exhibited reduced thrombosis compared to the group (($FeCl_3$+PC) administered with a *Polygunum cuspidatum* Sieb. et Zucc. extract or the group ($FeCl_3$+CC) administered with a *Cinnamomum cassia* Blume extract.

The invention claimed is:

1. An antithrombotic composition comprising *Polygonum cuspidatum* Sieb. et Zucc. and *Cinnamomum cassia* Blume as active ingredients.

2. The antithrombotic composition according to claim 1, wherein the *Polygonum cuspidatum* Sieb. et Zucc. and the *Cinnamomum cassia* Blume are an extract obtained by mixing in a weight ratio of 1:2-2:1 and through extraction.

3. The antithrombotic composition according to claim 2, wherein the *Polygonum cuspidatum* Sieb. et Zucc. and the *Cinnamomum cassia* Blume are an extract obtained by mixing in a weight ratio of 1:1 and through extraction.

4. The antithrombotic composition according to claim 2, wherein the extract is obtained by adding an extraction solvent at a volume that is 150 times to 250 times that of the mixture of the *Polygonum cuspidatum* Sieb. et Zucc. and the *Cinnamomum cassia* Blume, followed by immersion therein at 50° C. to 70° C. for 22 hours to 26 hours, thereby obtaining an extract, filtering the extract, concentrating the filtrate under reduced pressure, and drying the concentrate.

5. The antithrombotic composition according to claim 4, wherein the solvent is 70% ethanol.

6. An agent for preventing or treating thrombosis, the agent comprising the composition of claim 1 as an active ingredient.

7. An antithrombotic health food comprising the composition of claim 1.

* * * * *